(12) United States Patent
Schulz et al.

(10) Patent No.: US 7,617,744 B2
(45) Date of Patent: Nov. 17, 2009

(54) TRANSMISSION FOR TORQUE TRANSFER WITH AXIAL COMPLIANCE

(75) Inventors: Bradley D. Schulz, Savage, MN (US); Paul J. Leska, Sr., Chanhassen, MN (US); Dennis J. Willis, Bloomington, MN (US); Harold F. Fahrendorff, Golden Valley, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 196 days.

(21) Appl. No.: 11/332,407

(22) Filed: Jan. 13, 2006

(65) Prior Publication Data

US 2007/0163340 A1    Jul. 19, 2007

(51) Int. Cl.
  *G01N 19/00*  (2006.01)
(52) U.S. Cl. ................................ 73/865.9
(58) Field of Classification Search ............ 73/788, 73/865.6, 865.9
  See application file for complete search history.

(56) References Cited

U.S. PATENT DOCUMENTS

| 3,658,143 A | 4/1972 | Schwartz | 177/208 |
|---|---|---|---|
| 4,196,635 A * | 4/1980 | Zuber et al. | 73/794 |
| 2005/0056099 A1 | 3/2005 | Zubok et al. | 73/804 |
| 2005/0241404 A1 | 11/2005 | Salvesen | 73/788 |
| 2007/0161872 A1* | 7/2007 | Kelly et al. | 600/300 |

OTHER PUBLICATIONS

PCT International Search Report for International Application No. PCT/US2007/00726 mailed Sep. 26, 2007.
International Preliminary Report on Patentability PCT/US2007/000726 mailed Jul. 24, 2008.

* cited by examiner

*Primary Examiner*—Hezron Williams
*Assistant Examiner*—Tamiko D Bellamy
(74) *Attorney, Agent, or Firm*—Westman, Champlin & Kelly, P.A.

(57) ABSTRACT

A transmission for torque transfer with axial compliance and a test machine employing the transmission has a flexible connector that provides high torsional stiffness and high axial compliance while inducing no frictional forces. The transmission includes an axial portion allowed to translate freely along its axis due to a high axial compliance of the transmission while the transmission simultaneously facilitates rigid torque transfer.

25 Claims, 5 Drawing Sheets

TRANSMISSION FOR TORQUE TRANSFER WITH AXIAL COMPLIANCE

FIELD

The embodiments of the present invention relate to the field of transmissions for torque transfer, and to machines that employ such transmissions, such as orthopedic device wear test machines.

BACKGROUND

There are many applications in which a transfer of torque is required. In many devices, it is desirable to transmit pure torque through a machine component with high torsional stiffness in a very controlled and repeatable manner.

For example, testing machines, such as orthopedic device wear testing machines, will often have a component to which torque is applied repeatedly. After a number of cycles in which torque is transmitted to the orthopedic device implant, numbering in the millions, for example, wearing of the orthopedic device implant test specimen is determined. It is critical in such testing machines that the torque be transmitted with little deflection related error and be repeatable. In an orthopedic device implant wear testing machine, for example, a plurality of test stations are provided in which test specimens are tested. A precise and consistently repeatable torque transmission must be applied to each of the test specimens over the millions of test cycles so that each of the test specimens are subjected to the same wear conditions. Otherwise, the validity of the testing will be in question.

In certain devices, such as in orthopedic device wear test machines, a torque transfer transmission to provide precise force and motion control and rigid torque transfer along with axial loading. One such orthopedic device wear testing machine is a spinal implant wear test machine. In such a machine, for example, axial loading is provided on the spinal implant under test, and a torque is also applied to the test specimen. In such devices, it is desirable to provide high torsional stiffness with little deflection related error, while at the same time providing low axial stiffness so that cross-talk is not seen at the load cell.

SUMMARY

There is a need for a transmission for torque transfer that allows the transmission of pure torque to a machine component with high torsional stiffness and high axial compliance. There is also a need for an orthopedic device test machine that employs a torque transmission that is axially complaint and torsionally stiff to provide rigid torque transfer to a rotational element with axial compliance to allow substantially friction free axial translation of the rotational element.

These and other needs are met by embodiments of the present invention which include a transmission for torque transfer with axial compliance comprising a rotational element configured for rotation with respect to a non-rotational element. The rotational element has an axis of rotation and is movable axially along the axis of rotation with respect to the non-rotational element and is rotatable around the axis of rotation. A rotational transfer link is provided that is rotatable about the axis of rotation and is drivable by an actuator. A flexible connector is coupled between the rotational transfer link and the rotational element. This flexible connector is flexible along the axis of rotation and is torsionally stiff so as to rigidly transfer torque between the rotational transfer link and the rotational element without inducing friction to the relative axial movement between the rotational element and the non-rotational element.

The earlier stated needs are also met by other embodiments of the invention which include a testing machine comprising a test station having: an axial force applicator with an actuator element that applies a controlled axial force to a test specimen and is axially movable substantially frictionlessly; and a torque transmitter that rotates the actuator element substantially frictionlessly to apply a controlled torque to the test specimen through the axial force applicator.

The earlier stated needs are further met by other embodiments of the present invention which provide an orthopedic device test machine comprising at least one test station comprising: a rotational element configured to apply forces to an orthopedic device test specimen, and a torque transmission coupled to the rotational element and is axially compliant and torsionally stiff so as to provide rigid torque transfer to the rotational element while allowing substantially free axial translation of the rotational element.

The foregoing and other features, aspects and advantages of the described embodiments will become more apparent from the following detailed description and accompanying drawings.

DETAILED DESCRIPTION

The embodiments of the present invention address and solve problems related to the providing of pure torque to a machine component with high torsional stiffness and high axial compliance, without inducing frictional forces. Such a torque transfer transmission is especially useful in testing machines, such as orthopedic device testing machines, including spinal implant wear testing machines. The embodiments of the invention provide precise force and motion control by employing a torque transmission that transmits pure torque to a machine component with high torsional stiffness and high axial compliance. A rotational element is configured for rotation with respect to a non-rotational element. This rotational element has an axis of rotation and is movable axially along the axis of rotation with respect to the non-rotational element. A rotational transfer link is provided that is rotatable about the axis of rotation and is drivable by an actuator. A flexible connector is coupled between the rotational transfer link and the rotational element. This flexible connector is flexible along the axis of rotation, but is torsionally stiff so as to rigidly transfer torque between the rotational transfer link and the rotational element. It does this without inducing friction to the relative axial movement between the rotational element and the non-rotational element. When the torque transfer transmission is coupled to a friction free axial actuator, as in certain embodiments, the transmission provides a friction free axial/torsion actuation system. The axial portion in the system is allowed to translate along its axis freely due to the high axial compliance of the transmission while the transmission simultaneously facilitates rigid torque transfer.

Figures 1, 2:
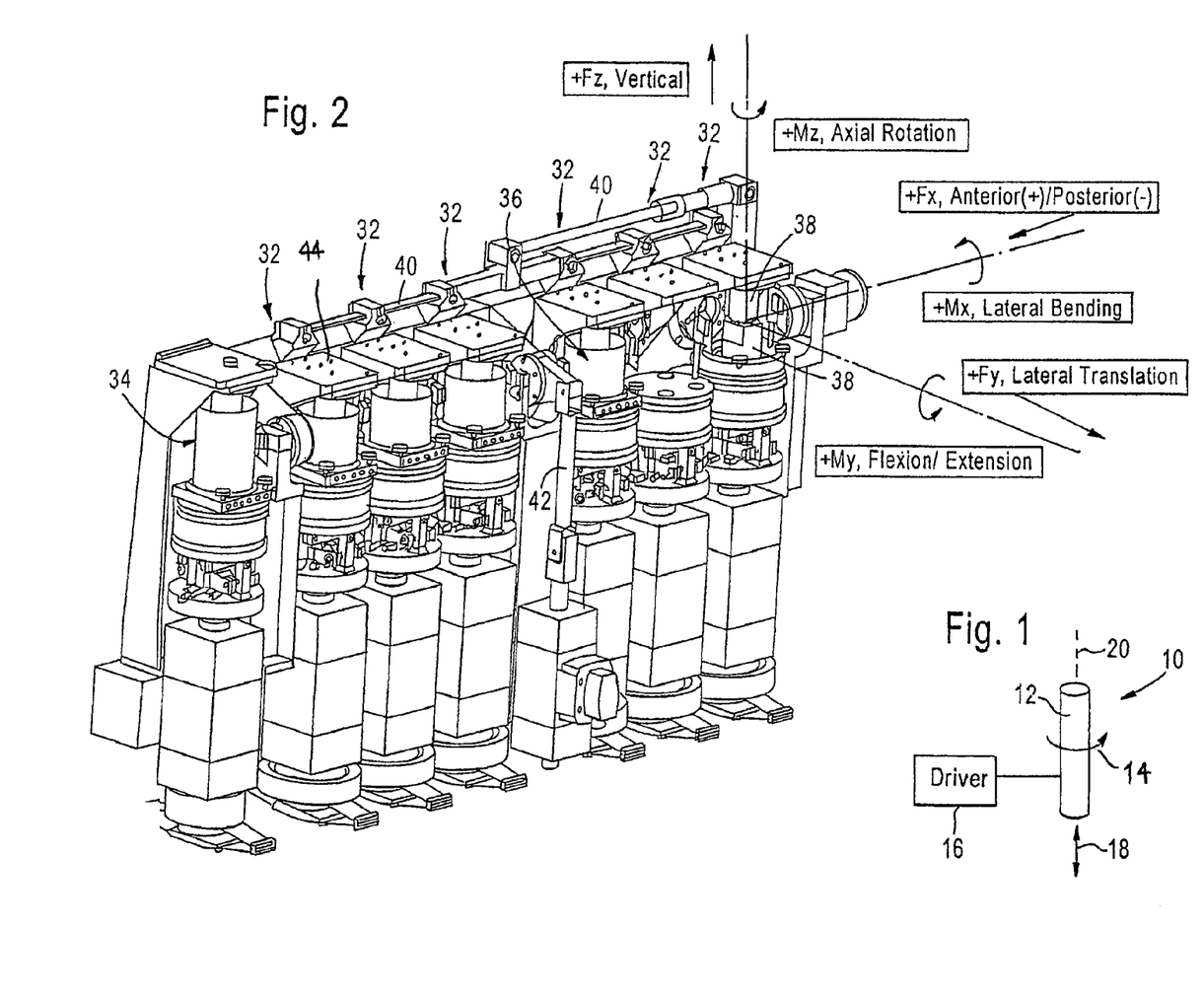
FIG. 1 is a schematic depiction of a torque transmitter depicting the transmission of the torque and axial compliance in accordance with embodiments of the present invention.
FIG. 2 is a perspective view of an exemplary test machine constructed in accordance with embodiments of the present invention, employing a transmission for torque transfer in accordance with embodiments of the present invention.

FIG. 1 is a schematic depiction of a torque transfer transmission with the direction of motions shown for explanation purposes. In FIG. 1, the torque transfer transmission 10 includes a rotational element 12 that rotates in the direction of arrow 14. The rotational element 12, such as a shaft, is driven by a driver 16. The arrows 18 schematically represent the axially compliant nature of the rotational element 12. In other words, the rotational element 12, in addition to its rotary motion 14 provided by driver 16, is able to freely translate along axis 20. As well, the rotational element 12 may also be controllably translated along axis 20, such as by a vertical force applicator (not shown). The axial compliance provided to the rotational element serves to prevent induction of frictional forces by the torque transmission. The axial compliance is important in order to limit the cross-talk onto the vertical load to a very small amount, and prevent cross-talk from being seen at a load cell, for example. At the same time, the transmission provided by the driver 16 to the rotational element 12 has high torsional stiffness, which is desirable to transmit drive torque with little deflection related error.

FIG. 2 shows a front perspective view of a test machine constructed in accordance with embodiments of the present invention, which employ a torque transfer transmission constructed in accordance with embodiments of the present invention. This test machine is exemplary only, as the torque transfer transmission may be employed in many other applications. However, this depiction of the test machine illustrates some of the features of embodiments of the present invention.

The test machine 30, which in this embodiment can be used for testing orthopedic devices, for example, has a plurality of test stations 32. In the illustrated embodiment, the test machine 30 is a spinal implant wear test machine, although it may be adapted for use in testing other orthopedic and prosthetic devices, or other types of devices. In the illustrated embodiment, there are six test stations 32 in which specimens are subjected to the forces applied by the machine 30, and a control station 34 that holds a specimen that is not subjected to all of the forces provided at the other test stations 32.

In the following description, the test machine 30 will be described as a spinal implant wear test machine for descriptive purposes, although it is to be clearly understood that this machine and the torque transfer or transmission may be employed in other applications. The test machine 30 is able to provide forces Fx, Fy and Fz in the x, y and z directions as depicted in FIG. 2, shown with the x, y and z axes at one of the test stations 32. Additionally, torques may be applied around the x, y and z axes, as depicted. The test specimen is not shown in FIG. 2 so as not to obscure the present invention. In a spinal implant wear testing machine, a specimen containment module 36 contains fluid in which the spinal implant test specimen is immersed. Upper and lower adapters 38 (only seen clearly at one of the test stations 36 in which the test chamber is removed for illustrative purposes) hold the test specimens between them within the containment module 36.

Briefly, the linkage 40 provides forces in the x direction with the linkage 42 providing forces in the y direction. The gimbals 44 connected to the upper adapters 38 may be moved around the y axis and around the x axis to provide moments around the x and y axes.

Figure 3:
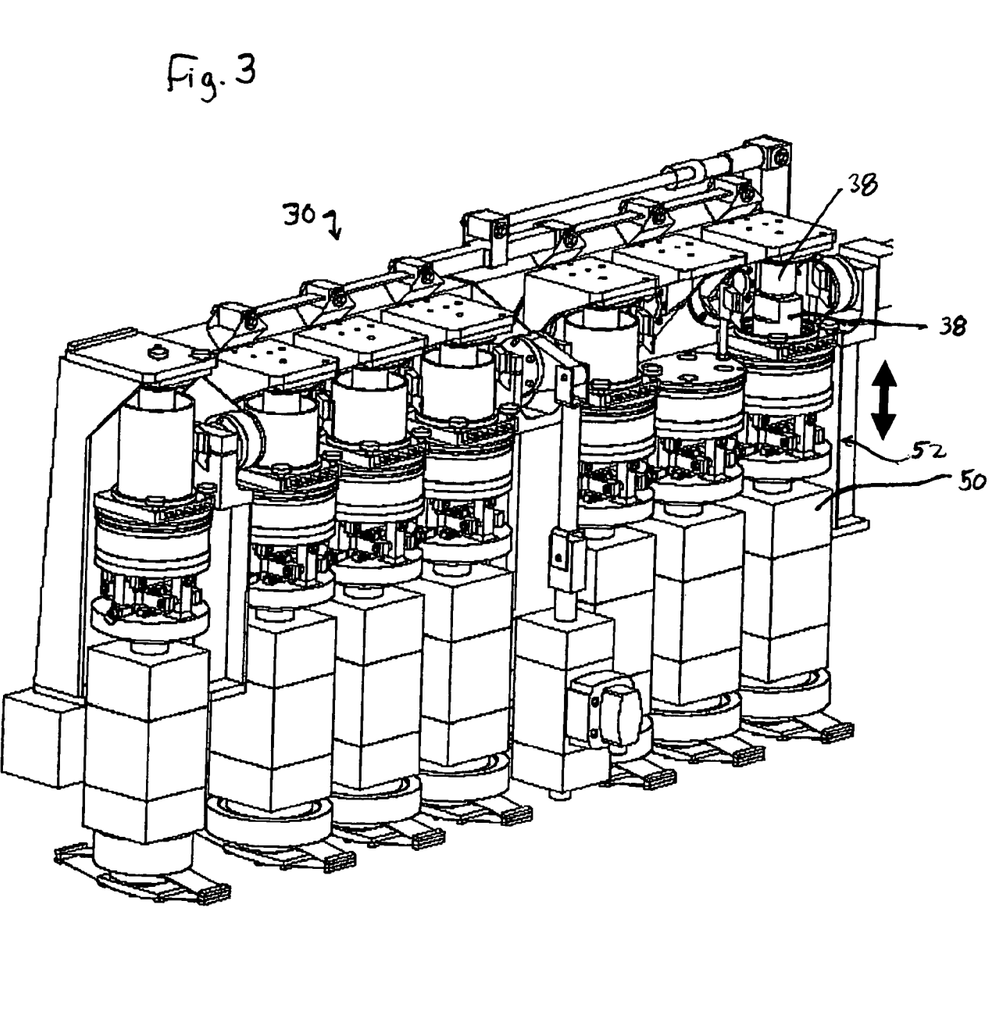
FIG. 3 schematically depicts the motion of vertical load actuators in the test machine of FIG. 3.

The vertical loads, represented by forces along the z axis, are provided by vertical load actuators 50, as shown in FIG. 3. Although different types of actuators may be employed, a friction free axial actuator is preferable to provide for a friction free axial/torsion actuation system. The vertical load actuator 50 applies a vertical loading along the z axis through components 52 to the test specimen (not shown) via the lower adapter 38. In the illustrated embodiment, the components 52 include an x-y slide table and a load cell.

Figure 4:
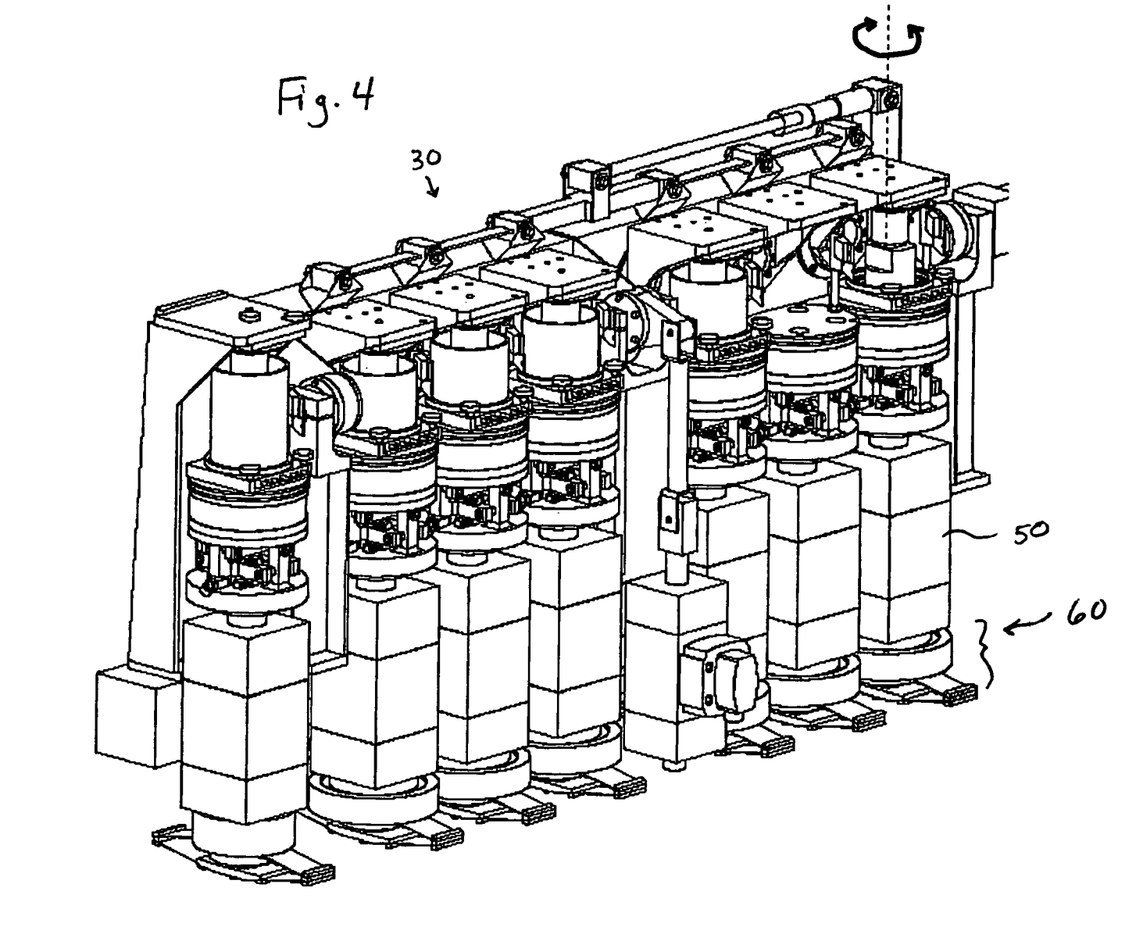
FIG. 4 schematically depicts axial rotation motion in accordance with embodiments of the present invention.

As described earlier, it is desirable to provide a transmission of drive torque with little deflection related error, having high torsional stiffness. At the same time, a low axial stiffness is desirable so that there is little cross-talk onto the vertical loading and so that cross-talk is not seen at the load cell. FIG. 4 highlights the axial rotation linkage 60 which is coupled to the actuator 50. The motion of the axial rotation linkage 60 is around the vertical axis z, as depicted in FIG. 4. Although the axial rotation linkage 60 is depicted at the bottom of FIG. 4, it should be apparent to those of skill in the art that the structure depicted in FIG. 4 is suspended vertically so that the axial rotation linkages 60 are free to rotate.

Figure 5:
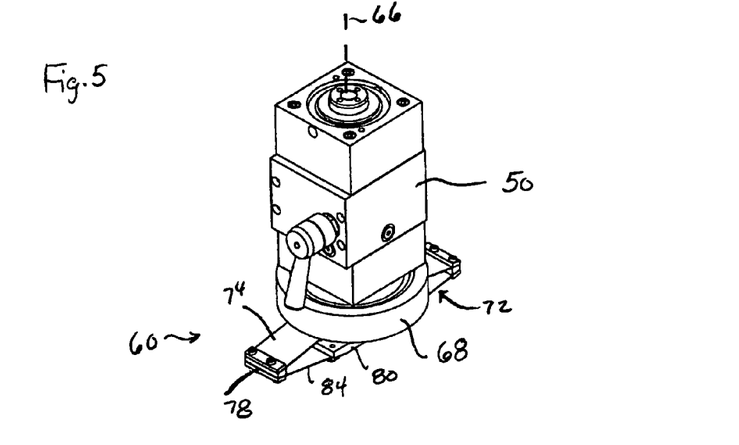
FIG. 5 is a perspective view of a torque transfer transmission constructed in accordance with embodiments of the present invention, shown in isolation.
Figure 6:
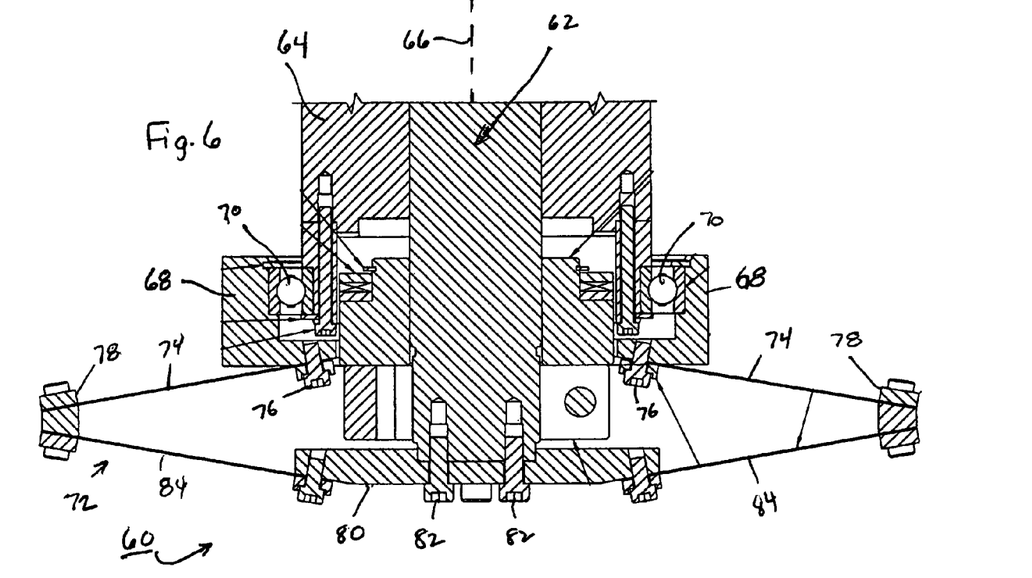
FIG. 6 is a cross-sectional view of one embodiment of a transmission for torque transfer.

An isolated view of an embodiment of an axial force actuator 50 with axial rotation linkage 60 is depicted in FIG. 5. A cross-sectional view of the torque transmitter (or transmission for torque transfer) is depicted in FIG. 6. Both figures will be referred to in the following.

The torque transfer transmission 60 includes a rotational element 62, such as an actuator rod 62, that is configured for rotation and axial movement with respect to a stationary (non-rotational) element. In this case, the actuator housing 64 serves as the non-rotational element. The actuator rod 62 has a central axis of rotation 66.

The axial force applicator 50 in preferred embodiments is a friction free axial actuator. Such a friction free axial actuator, combined with the torque transfer transmission of the present invention, provides a friction free axial/torsion actuation system. The actuator rod 62 is allowed to translate along axis 66 freely due to the friction free nature of the axial force applicator, as well as the axial compliance of the torque transfer transmission in accordance with embodiments of the invention. Examples of friction free axial force applicators are known to those of skill in the art. Although not perfectly frictionless, in such an actuator the friction is extremely low and is due only to viscous oil shear.

It is desirable to provide for a torque transfer to the actuator rod 62 with high torsional stiffness while not inducing frictional forces to the actuator rod 62. The torque transfer transmission 60 achieves this by providing a flexible connector 72 that is torsionally stiff and axially compliant. A rotational transfer link 68 is rotatably mounted at the bottom of the actuator 50. In the embodiment depicted in FIGS. 5 and 6, the rotational transfer link 68 is annularly shaped and rotates around the central axis 66. The rotational transfer link 68 is mounted on bearings 70 that allow free rotation of the rotational transfer link 68.

The torque transfer transmission 60 includes the flexible connector 72 (or "axially compliant element") that is coupled between the rotational transfer link 68 and the rotational element (actuator rod) 62. The flexible connector 72 is axially compliant so that it is flexible along the axis of rotation. At the same time, the flexible connector 72 is torsionally stiff so as to rigidly transfer torque between the rotational transfer link 68 and the rotational element (actuator rod) 62.

In embodiments of the invention, such as those depicted in FIGS. 5 and 6, the flexible connector 62 includes a plurality of flexible elements, such as flexure plates. A first flexure plate 74 is attached to the rotational transfer link 68, such as by fastener 76. The first flexure plate 74 extends at an angle away from the rotational transfer link from a first end to connect at a second end to a connector 78.

A shaft coupler 80 is coupled to the actuator rod 62 by fasteners 82, for example. Second flexure plates 84 are coupled to the shaft coupler 80 at one end, and extend outwardly at an angle from the shaft coupler to the connector 78. The first and second flexure plates are thereby connected at their second ends to the connector 78.

As seen in FIGS. 5 and 6, two pairs of first and second flexure plates 74, 84 may be arranged 180° from one another. Additional pairs of flexure plates may also be provided in the same plane.

In other embodiments, additional flexible connectors 72 may be provided in series so as to increase axial compliance while maintaining high torsional stiffness.

The embodiments of the present invention that are illustrated depict flexure plates as the flexible connector 72. However, other types of flexible connectors 72 may be employed without departing from the scope of the present invention. For example, flexible billows may be used or other arrangements that provide a flexible connection that is torsionally stiff while being axially compliant.

Figure 7:
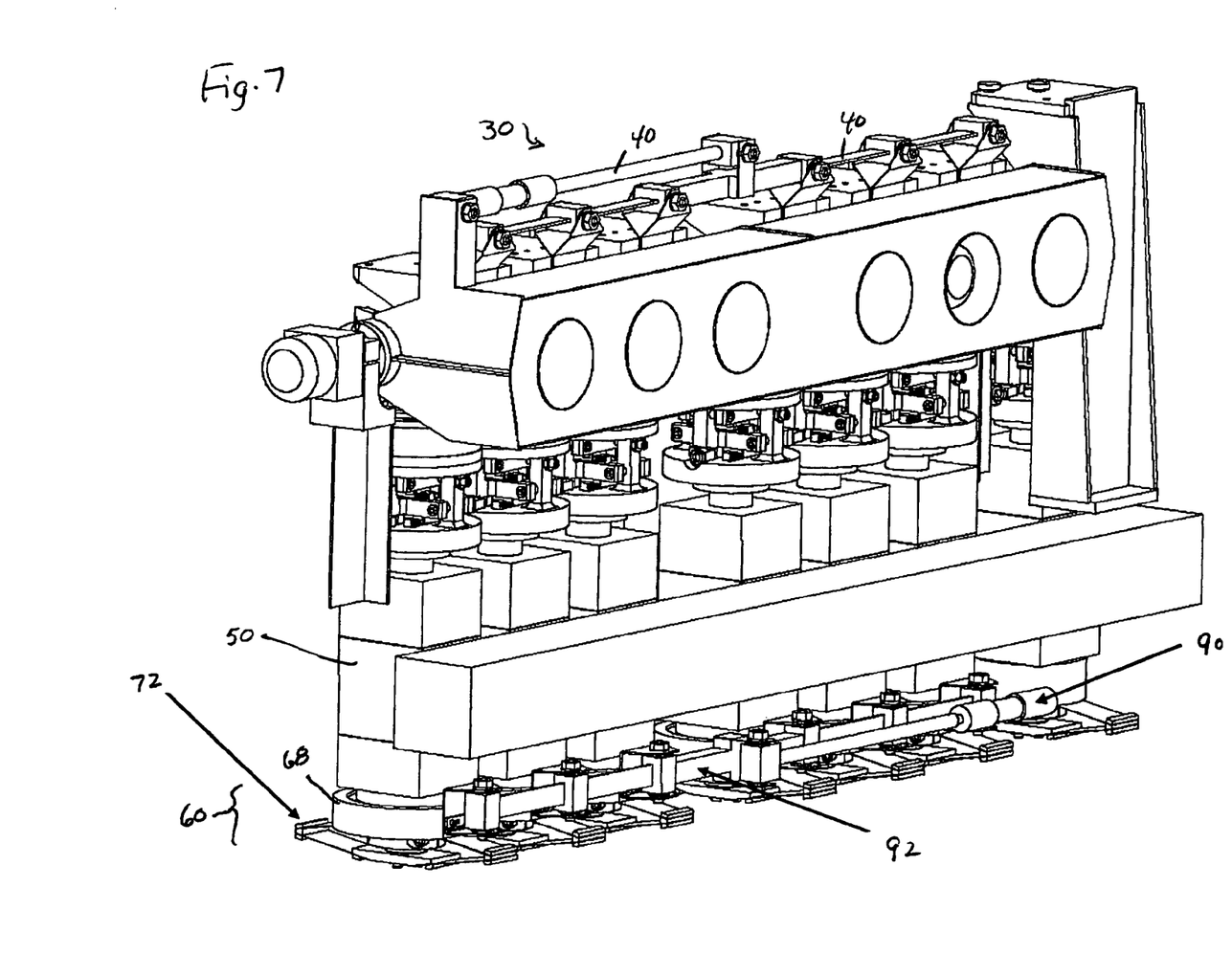
FIG. 7 shows a rear view of the test machine of FIGS. 2-4.

A rear view of the test machine 30 is depicted in FIG. 7. A linear actuator 90 operates via a connecting link 92 to drive the plurality of rotational transfer links 68 simultaneously. The linear motion imparted to the connecting link 92 is translated to a rotational motion at the connection to the rotational transfer links 68 at the test stations 32. Hence, all of the rotational transfer links 68 are precisely and simultaneously driven. The axial compliant nature of the torque transfer transmission assures that friction forces do not interfere with providing the same torque to each of the test specimens.

In operation of the test machine 30, the forces in the x and y directions and moments around the x and y axes may be applied and controlled independently from the vertical force application (shown in FIG. 3), as well as the axial rotation (shown in FIG. 4). A friction free axial/torsion actuation is provided by the illustrated arrangement. The axial force applicator 50 applies a load to the test specimen along the z-axis by moving the actuator rod 62 along the z-axis. Driven by linear actuator 90 through the connecting link 92, the rotational transfer link 68 and the flexible connector 72 facilitate rigid torque transfer to the actuator rod 62 to the test specimen (not shown) at the test station 32. The actuator rod 62 is allowed to translate along its axis 66 freely due to the high axial compliance provided by the flexible connector 72 of the torque transfer transmission 60. The arrangement may be used with precise force and motion control applications, such as in test machines for testing wear of orthopedic and prosthetic devices. The arrangement may also be used in other devices in which a torque transfer is desired without inducing frictional forces.

Although embodiments of the present invention have been described and illustrated in detail, it is to be clearly understood that the same is by way of illustration and example only and is not to be taken by way of limitation, the scope of the present invention being limited only by the terms of the appended claims.

What is claimed is:

1. A testing machine comprising:
   a torque transmission assembly configured to supply a load to a test specimen including a rotational portion rotationally disposed relative to a non-rotational portion and axially movable along a rotation axis, a transmission portion including a rotational transfer link rotationally coupled to the non-rotational portion and coupled to the rotational portion through a connector assembly to transmit torque from the transmission portion to the rotational portion and the connector assembly including at least one axially compliant linkage to allow axial movement of the rotational portion relative to the non-rotational portion.

2. The testing machine of claim 1, wherein the rotation axis is a vertical axis and the transmission portion is coupled to the non-rotational portion to rotate the rotational portion around the vertical axis.

3. The testing machine of claim 1, and comprising coupler portion coupled to the rotational portion, and the axially compliant linkage is coupled between the rotational transfer link and the coupler portion.

4. The testing machine of claim 3 wherein the axially compliant linkage includes at least one pair of flexure plates, with a first flexure plate attached at a first end to the rotational transfer link and extending outwardly from the rotational transfer link and having a second end, with a second flexure plate attached at a first end to the coupler portion and extending outwardly from the coupler portion and having a second end coupled to the second end of the first flexure plate.

5. The testing machine of claim 1 further comprising a plurality of the test stations for testing a plurality of test specimens and including a plurality of torque transmission assemblies to supply loads to the plurality of test specimens.

6. The testing machine of claim 1, wherein the testing machine is an orthopedic device wear testing machine.

7. The testing machine of claim 1 wherein the axially compliant linkage includes a plurality of flexure elements connected in series.

8. An orthopedic device test machine, comprising:
   a rotational element rotationally supported in a housing and movable along a rotation axis to apply a load to an orthopedic device test specimen secured to the orthopedic device test machine; and
   a torque transmission assembly including a rotational transfer link rotationally coupled to the housing and at least one flexure element operably connecting the rotational element to the rotational transfer link to transfer torque to the rotational element wherein the at least one flexure element allows for axial movement of the rotational element relative to the rotational transfer link.

9. The orthopedic device test machine of claim 8 wherein the rotational element is configured to supply an axial force to the orthopedic device test specimen.

10. The orthopedic device test machine of claim 8 wherein the torque transmission assembly includes at least one pair of flexure plates operably connecting the rotational transfer link to the rotational element and the at least one pair of flexure plates includes with a first flexure plate attached at a first end to the rotational transfer link and extending outwardly from the rotational transfer link and having a second end, with a second flexure plate coupled at a first end to the rotational element and extending outwardly from the rotational element and having a second end coupled to the second end of the first flexure plate.

11. The orthopedic device test machine of claim 8 further comprising a plurality of the flexure elements coupled in series.

12. The testing machine of claim 1 and comprising a holder assembly configured to hold the test specimen.

13. The testing machine of claim 1 wherein the rotational portion includes an actuator rod slideably disposed in the non-rotational portion.

14. The testing machine of claim 1 wherein the rotational transfer link is rotationally coupled to the housing by a bearing assembly.

15. The testing machine of claim 1 and further comprising a linear actuator coupled to the rotational transfer link to rotate the rotational transfer link to provide torque input to the rotational portion.

16. The testing machine of claim 1 in combination with an actuator to impart an axial force to the test specimen along the rotation axis.

17. The test machine of claim 8 wherein the rotational transfer link is translationally fixed to the housing and rotationally coupled to the housing through a bearing assembly.

18. The test machine of claim 17 and comprising a plurality of flexure elements connected in series to operably connect the rotational transfer link to the rotational element.

19. A testing apparatus comprising:
 a rod rotatable within a housing about a rotation axis and axially movable along the rotation axis;
 a transmission assembly configured to impart rotation to the rod to impart a load input to a test specimen; and
 a flexure assembly connecting the rod to the transmission assembly to provide axial compliance between the rod and the transmission assembly.

20. The testing apparatus of claim 19 and comprising at least one holder assembly to hold the test specimen for testing.

21. The testing apparatus of claim 19 wherein the flexure assembly includes a first flexible body connected to the transmission assembly and a second flexible body connected to the rod and the first and second flexible bodies are connected in series to provide the axial compliance between the rod and the transmission assembly.

22. The testing apparatus of claim 21 wherein the first and second flexure bodies are formed of first and second flexure plates.

23. The testing apparatus of claim 19 wherein the transmission assembly includes a rotational transfer link and including a first flexure assembly connected to the rotational transfer link and a second flexure assembly connected to the rotational transfer link about 180 degrees from the first flexure assembly.

24. The testing apparatus of claim 19 wherein the transmission assembly includes a rotational transfer link rotationally coupled to the housing and the flexure assembly includes a flexure body connecting the rotational transfer link to the rod.

25. The testing apparatus of claim 24 and comprising a linear actuator configured to impart a rotation to the rotational transfer link.

* * * * *

UNITED STATES PATENT AND TRADEMARK OFFICE
CERTIFICATE OF CORRECTION

PATENT NO. : 7,617,744 B2
APPLICATION NO. : 11/332407
DATED : November 17, 2009
INVENTOR(S) : Schulz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 456 days.

Signed and Sealed this

Nineteenth Day of October, 2010

David J. Kappos
*Director of the United States Patent and Trademark Office*